United States Patent [19]
Roberts et al.

[11] Patent Number: 6,001,088
[45] Date of Patent: Dec. 14, 1999

[54] IONTOPHORESIS METHOD AND APPARATUS

[75] Inventors: Michael Stephen Roberts, Westlake; Sheree Elizabeth Cross, Tarragindi; Pam Muhtze Lai, Stretton; Lawrence William Hirst, St. Lucia, all of Australia

[73] Assignee: The University of Queensland, Queensland, Australia

[21] Appl. No.: 08/849,280

[22] PCT Filed: Dec. 4, 1995

[86] PCT No.: PCT/AU95/00816

§ 371 Date: Aug. 18, 1997

§ 102(e) Date: Aug. 18, 1997

[87] PCT Pub. No.: WO96/16693

PCT Pub. Date: Jun. 6, 1996

[30] Foreign Application Priority Data

Dec. 2, 1994 [AU] Australia ............................... PM 9826

[51] Int. Cl.$^6$ ...................................................... A61N 1/30
[52] U.S. Cl. ............................ 604/501; 604/21; 604/514; 607/134; 607/135
[58] Field of Search ............................ 604/20–21, 504, 604/514; 607/135–137, 141

[56] References Cited

U.S. PATENT DOCUMENTS

| | | |
|---|---|---|
| 109,367 | 11/1870 | Adams . |
| 1,740,240 | 12/1929 | Honey . |
| 2,123,980 | 7/1938 | Warwick . |
| 2,525,381 | 10/1950 | Tower . |
| 3,991,755 | 11/1976 | Vernon et al. . |

OTHER PUBLICATIONS

Bagniefski, T. and Burnette, R.R., 1990, j. Controlled Release 11 113–112.
Bellatone, N.H.; Rim, S., Francoeur, M.L. and Rasadi, B., 1986, Int. J. Pharmacol. 30 63–72.
Burnette et al., 1988, J. Pharm. Sci., 77 132–137.
Burnette, R.R Marrero, D., 1986, J. Pharm. Sci. 5 738–743.
Burnette, R.R. and Ongpipattanakul, B., 1987, J. Pharm. Sci., 76 765–773.
Chien et al., 1989, J. Pharm. Sci., 78 376–383.
DelTerzo et al., 1989, Pharm. Res., 6 85–90.
DeNuzzio, J.D. and Berner, B., 1989, J. Controlled Release, 11 105–112.
Feldman, R.J. and Maibach, H.I., 1967, Arch. Dermatol. 48 181–183.
Gangarosa et al., 1980, J. Pharm. Exp. Ther., 212 377–381.
Kasting, G.B. and Keister, J.C., 1989, J. Controlled Release, 8 1950210.
Kligman, A.M. & Christophers, E., 1963, Arch. Dermatol., 88 702–705.
Lelawongs et al., 1990, Int. J. Pharm., 61 179–188.
Masada et al., 1989, Int. J. Pharm., 49 57–62.
O'Malley, E.P. and Oester, Y.T., 1955, Arch. Phys. Med. Rehabil., 36 310–316.
Okabe et al., 1986, Controlled Release, 4 79–85.
Phipps et al., 1989, j. Pharm. Sci., 78 365–369.
Pikal, M.J., 1990, Pharm. Res., 7 213–221.
Pikal, M.J. and Shah, 1991, S. Pharm. Res. , 7 222–229.
Potts et al., 1984, J. Invest. Dermatol., 82 97.
Roberts et al., 1982, Aust. N.Z. J. Med., 12 305–306.
Siddiqui et al., 1985b, J. Pharm. Pharmacol., 37 732–735.

(List continued on next page.)

*Primary Examiner*—Mark Bockelman
*Attorney, Agent, or Firm*—Stroock & Stroock & Lavan LLP

[57] ABSTRACT

An iontophoresis method for delivenng an active substance or drug to a target tissue which includes the step of sandwiching the target tissue between a donor electrode and receptor electrode which are each electrically connnected to a power source wherein a current path between the donor electrode and the receptor electrode is maintained at a minimum value to enhance delivery of the active substance to the target tissue.

14 Claims, 9 Drawing Sheets

OTHER PUBLICATIONS

Siddiqui et al., 1985, Int. J. Pharm., 27 193–203.
Siddiqui et al., 1989, J. Pharm Pharmacol., 41 430–432.
Singh et al., 1993, J. Pharm. Sci 82 127–131.
Srinvasan et al., 1989, J. Pharm. Sci. 78 370–375.
Tregear, 1966, J. Invest. Dermatol. 46 16–23.

Wearley et al., 1989, J. Controlled Release 9 231–242.

Yamamoto, T. & Yamamoto, Y., 1976, Med. Biol. Eng. Comp. 14 151–158.

Yamamoto, T. & Yamamoto, Y., 1978, Med. Biol. Eng. Comp. 16 592–594.

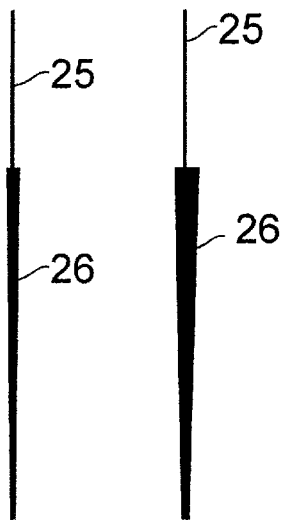
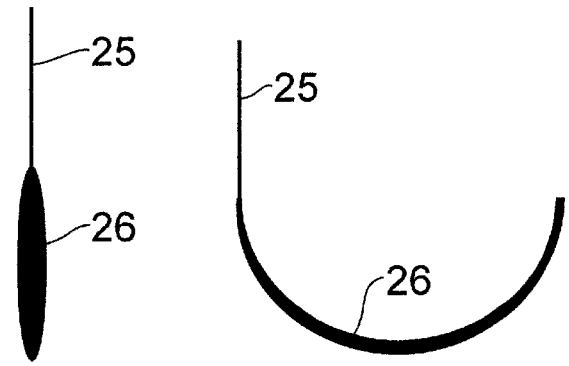
FIG. 2A  FIG. 2B  FIG. 2C
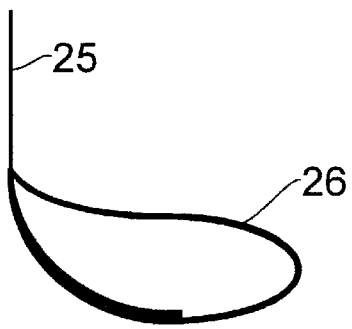
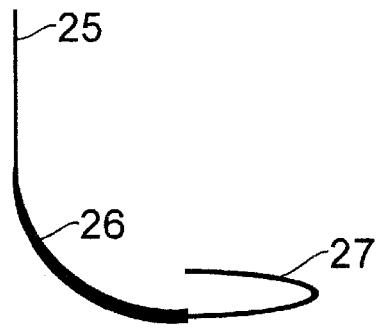
FIG. 2D  FIG. 2E
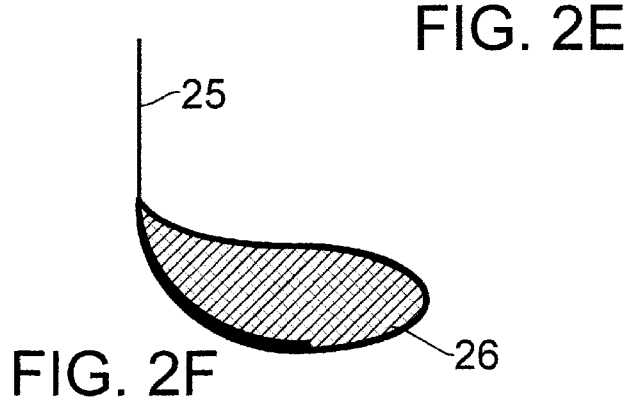
FIG. 2F

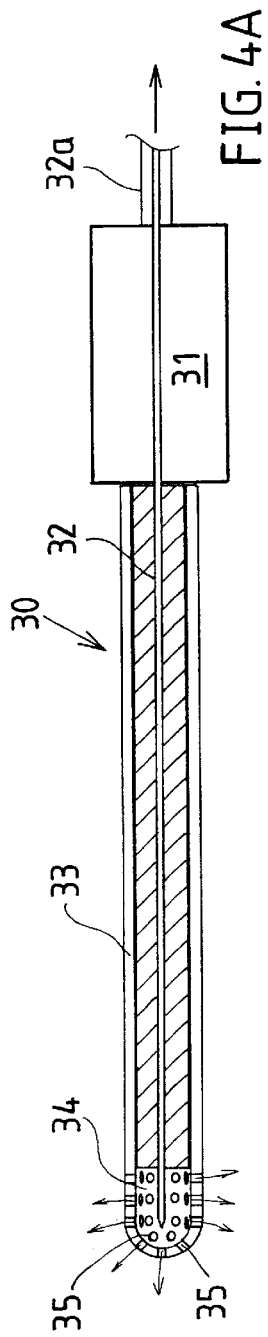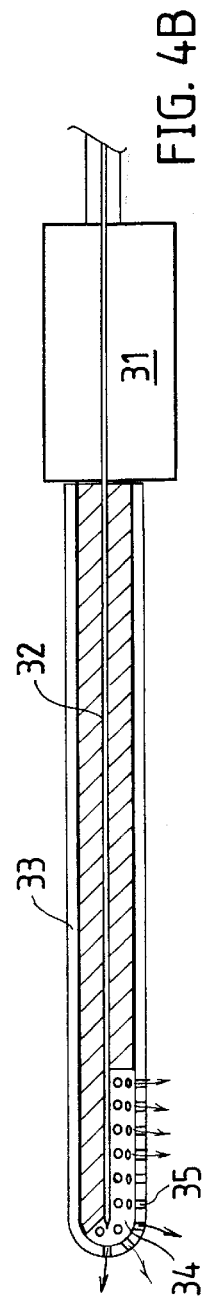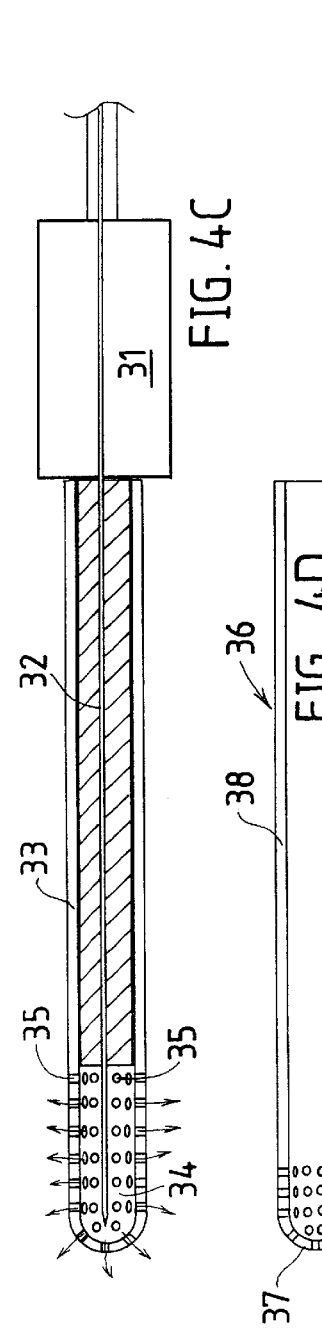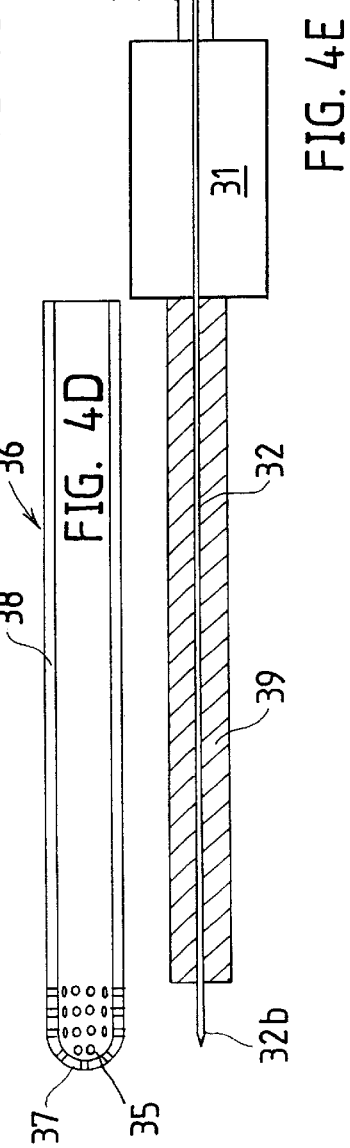

IONTOPHORESIS METHOD AND APPARATUS

FIELD OF THE INVENTION

THIS INVENTION relates to the process of iontophoresis whereby the delivery of topical active agents is enhanced by the application of an electrical potential difference.

Iontophoresis targets active agents to tissues underlying the skin such as the dermis, subcutaneous tissue, fascia or muscle, bypassing the gastrointestinal tract as a site of absorption and hence avoiding first pass degradation of the drug.

BACKGROUND OF THE INVENTION

The skin is the major barrier to the entry of foreign solutes from the environment into the body as well to the loss of heat and moisture from the body. The outermost layer of the epidermis, the stratum corneum, is normally assumed to be the major barrier to drug absorption through the skin. It has also been assumed that the drugs penetrating the epidermis are then removed by the dermal blood supply.

Drugs will not penetrate into deeper tissues after topical application if the stratum corneum barrier is not overcome. Complete removal of this barrier should yield tissue levels equivalent to those observed after dermal application. Singh et al., (1993) referred to in the list of references hereinafter, observed that iontophoresis also yielded tissue concentrations of lignocaine and salicylic acid in vivo, similar to those observed for dermal application.

Iontophoresis is a process which involves the transport of charged substances into body tissue, such as skin, by the passage of an electric current. Transport of solutes by iontophoresis is dependent on many factors, including solute physio chemical factors which includes (ionic charges [Gangarosa et al., 1980; Pikal, 1990; Srinivasan and Higuchi, 1990; Kasting and Keister, 1989; Phipps et al., 1989; Burnette and Ongpipattanakul, 1987; DeNuzzio and Berner, 1990], the presence of extraneous ions [Bellatone et al., 1986], pH of the donor solution [Siddiqui et al., 1985b and 1989; Burnette and Marrero, 1986; Wearley et al., 1989], ionic strength [Lelawongs et al, 100-; Wearley et al., 1989], solute concentration [O'Malley and Oester, 1955; Bellatone et al, 1986; Wearley et al., 1989], buffer constituents, chemical structure of the solute inclusive of conductivity [Siddiqui et al., 1989]); physiological factors (skin region—density of appendages [Roberts et al., 1982; Feldman et al., 1967], age, sex, race, hydration of the skin [Potts et al., 1984], delipidization—ethanol pretreatment [Srinivasan et al., 1989], fluidisation of lipids and permeability of skin [Tregear, 1966; Phipps et al., 1989]) and electrical factors inclusive of current density [Bellatone et al., 1986; DelTerzo et al., 1989], nature of electrodes [Bellatone et al., 1986, Masada et al., 1989], duration of treatment, nature of current [Okabe et al., 1986; Yamamoto and Yamamoto, 1976 and 1978; Chien et al., 1989; Bagniefski and Burnette, 1990; Pikal and Shah, 1991]).

Hitherto there has been described methods and compositions for enhanced skin concentration of iontophoretically delivered active agents. During iontophoresis, charged compounds pass from a reservoir attached to the skin of a person into the tissue underneath. The process is one wherein the rate of delivery is a function of current, active agent concentration and presence of other ions. It is a generally held belief that higher concentrations of active agent, higher levels of current and lower concentrations of other ions result in greater delivery of the active compound. Generally, iontophoretic devices comprise at least two electrodes—both on the surface, an electrical energy source, such as a battery, and at least one reservoir which contains the active agent to be delivered.

Mention can be made to prior art which describes methods and devices involving the internal placement of iontophoretic electrodes into body cavities. Stephen et al., (U.S. Pat. No. 5,222,936) describe a method and apparatus specifically for the placement of an iontophoretic electrode in the form of a tubular catheter into hollow body cavities containing ion-rich physiological fluids, such as the bladder and vagina. The purpose of their invention was to introduce a technique whereby the selection of the active electrode material and drug counterion would be such as to produce ionic species which interact with one another to minimise or reduce the number or water hydrolysis products produced by electrode decay as a result of the iontophoretic process.

Reference can also be made to German Patents 3809814 and 3844518 which describe electrodes designed for implantation into fluid containing hollow body cavities, specifically the bladder, for the local treatment of bladder cancer by iontophoresis. In these specifications, the receptor electrode was enclosed in a type of girdle worn around the lower part of the body and connected to the electrode placed in the bladder. The electrode placed in the bladder comprised a tubular rigid probe having a peripheral wall and opposed rows of delivery apertures in the peripheral wall. The inserted end of the probe was sealed and a conductor passed down the hollow interior of the probe and was connected to a source of current at an outer end.

U.S. Pat. No. 4,411,648 also refers to electrode placement in the bladder to prevent infection. In this case, both donor and receptor electrodes in the form of rigid metal probes were inserted into the bladder and the surrounding bladder contents were sterilised by the ions generated by the decomposition of the electrode when the current was passed. All of the abovementioned references rely upon the presence of a fluid environment around their donor electrodes for the passage of drug solution or generation of heavy metal ions and were specifically concerned with delivery of the drug solution to the relevant body cavity.

Reference may be made to other prior art concerning location of one electrode on the skin of a subject and the location of another electrode such as a probe or needle electrode in a body cavity or body tissue which is described in International Publication WO94/05369. This specification describes a probe type electrode which may have a needle or trocar attached thereto which has a selectively permeable membrane through which a drug may be driven by a voltage gradient to deliver a drug to a target area of an internal body tissue. The iontophoresis apparatus described in this reference may be utilised to deliver a drug to a tumour. International Publication WO91/16945, International Publication WO94/05361 and U.S. Pat. No. 3,491,755 describe similar iontophoresis apparatus.

Reference may also be made to EP 0438078 which describes a probe electrode or catheter having an internal cavity in which is located an internal wire electrode and a plurality of holes or apertures in a side wall of the cavity to allow for passage of a drug from an internal cavity to a body cavity or organ. A counter-electrode may be placed on the outside of the body on the skin as close as possible to the organ subjected to the iontophoretic treatment.

FR 2516388 describes a similar probe electrode or catheter to that described in EP 0438078 which may be fitted with a needle in the catheter for iontophoresis injection into physiological joints. The catheter may be provided with internal electrodes spaced from each other and located in a side wall of the catheter and flush with an internal surface of the side wall.

Reference also may be made to EP 0378132 which refers to iontophoresis needle electrodes.

In summary of the abovementioned prior art, it will be appreciated that the donor or active electrode which was responsible for drug delivery and the receptor or inactive electrode has been utilised in a variety of situations which include:

(i) adjacent each other in topical applications such as the epidermis;

(ii) the active electrode being inserted in a body cavity while the inactive electrode was placed on the skin; or (iii) where both electrodes were inserted in the same or different body cavities.

However, it has now been discovered that an iontophoresis technique may be applied for effective administration of a drug to sensitive tissues such as the eye, ear inclusive of the eardrum, nose or throat in a non-invasive manner to avoid the use of invasive administration techniques such as direct injection of the drug into the sensitive tissue which is often painful or traumatic and is also risky because, if not administered satisfactorily, may result in serious injury.

SUMMARY OF THE INVENTION

It therefore is an object of the invention to provide a method of use of iontophoresis apparatus which may allow administration of an active substance, such as a drug, to sensitive tissues in a non-invasive manner.

The invention, therefore, refers to a method of administration of an active substance to a sensitive target tissue selected from the eye, ear, nose or throat which includes the step of insertion of a first electrode in a nasal passage of a subject and application of a second electrode to the subject adjacent the eye or adjacent the ear wherein said first and second electrodes are each electrically connected to a power source and said target tissue is sandwiched between each of said electrodes to achieve a current path which is of minimal electrical resistance.

The first electrode or the second electrode may act as a donor electrode (to deliver the active substance) or as a receptor, electrode (to complete the circuit) as desired. It will be understood by the skilled person that when the first electrode acts as a donor electrode, the second electrode is required to act as a receptor electrode, and vice versa. Preferably, the first electrode is the donor electrode in which case the second electrode is the receptor electrode.

The field of the present invention will also include the iontophoresis of drugs into tissue using a needle electrode. This technique differs from that of MENS, the application of therapeutic electrical currents to muscle between electrodes which is used in physiotherapy as the method of the present invention requires the delivery of an active drug substance by the applied current, which is also of a different power and frequency. Thus, normally the current utilised in the iontophoretic method of the invention may be 0.05–5.0 milliamp/sq cm.

Examples of drugs or therapeutic substances that may be used as an active agent in the apparatus of the invention include non-steroidal anti-inflammatory agents (NSAIDS) which, when taken orally, may cause irritation of the stomach or intestine, permeation enhancers, buffers, bacteriostatics, antioxidants, anaesthetics, hormones, anti-arthritics, anti-virals, antineoplasics, anti-inflammatories, muscle relaxants, antihistamines, antibiotics, and corticosteroids.

Specific examples of antibiotics include clindamycin, spectromycin and vancomycin. Specific examples of suitable corticosteroids include hydrocortisone and dexamethasone.

The active agent may also include any biologically active compounds or mixture of compounds that have therapeutic, prophylactic, pharmacological, physiological effect on a subject and may also include one compound or mixture of compounds that produce more than one of these effects.

Vehicles or excipients which may be used in the apparatus of the invention include any non-toxic aqueous compound which is suitable for topical application and which are liquid at room temperature.

The type of electrodes utilised in the method of the invention may vary dependent upon the required application. If the donor electrode is to be applied topically, then such electrode will most commonly be in the form of a pad containing an active substance in solution having a backing metal plate or electrode. An example of such an electrode is the conventional gel type pad (such as IOMED). The donor electrode is usually placed on an outer body surface, such as skin, while the receptor electrode is an inserted electrode which may be a probe electrode suitably of the type hereinafter described or a needle electrode which is inserted directly into tissue. The use of a needle electrode as receptor electrode provides a distinct advantage over the probe type electrodes discussed above in that the probe type electrodes can only be inserted in body orifices or cavities and thus have only a limited application. In contrast, the needle electrode can be utilised or inserted directly into tissue and can also be inserted into body orifices and cavities.

The needle electrode utilised in the iontophoresis method of the invention may include a needle part having an outer end which is preferably pointed in the same manner as a syringe needle. The needle part may also include an insulating sheath adjacent to the outer end. The needle electrode may also include an electrode body made of any suitable metal such as platinum, silver or stainless steel. A conductor or wire may pass through the electrode body and thus current may travel along the wire and continue along the needle. The wire may be connected to a source of electrical current.

It will be found in practice that operation of the method of the invention especially when utilising the needle electrode may be used to target any tissue area included in the epidermis, dermis, subcutaneous tissue, fascia, muscle, fat pad, deep muscle, joints, bones, nerves and eyes. The administration of an active compound in accordance with the method of the invention travels to the target site or tissue more quickly than by oral administration and in higher concentrations. Another advantage of active agent administration using the method of the invention is essentially a localised application that will alleviate chronic pain.

The donor electrode, for use in the invention, may comprise an insertable probe electrode including an elongate probe body having an insert end including a compartment for containing the drug or active substance.

Suitably the compartment comprises a hollow space adjacent the insert end which is provided with access means for drug delivery. The access means may include a plurality of perforations or drug delivery apertures or alternatively, a porous sheath or. sleeve such as a dialysis membrane. The donor electrode may also include an insulating handle.

The donor electrode, in another embodiment, may include a detachable sheath including a number of perforations or drug delivery apertures at one end. The compartment may be formed when the sheath is attached to the probe body.

The probe body may be solid as shown but the compartment may replace all of the probe body if desired and thus terminate adjacent the insulating handle if required.

In another embodiment, the probe body may be flexible instead of rigid. Any suitable flexible material may be utilised such as elastomeric material such as synthetic or natural rubber or resilient plastics material. This is in contrast to the previously described embodiment where the probe body may be formed from rigid plastics material such as polycarbonate or polyethylene. Again, as in the previously described embodiment, the compartment may terminate adjacent the insulating handle if desired.

In another embodiment, the tip of the electrode may comprise a dialysis membrane if the electrode has to contact damaged, inflamed or sensitive tissue.

In the method of the invention, a probe electrode of the type described above may be inserted into the nasal passage where the insert end is in contact with tissue adjacent the eye as shown in the preferred embodiment. The receptor electrode may be in bearing contact with a part of the eye as shown (e.g. eyelids, eyebrows, conjunctiva).

It will be appreciated in this embodiment that the donor electrode may be inserted into an ear cavity in substitution of a nasal cavity if desired.

BRIEF DESCRIPTION OF THE DRAWINGS

Reference may now be made to a preferred form of the invention as shown in the attached drawings, wherein:

FIGS. 2A, 2B, 2C, 2D, 2E and 2F illustrate various forms of needle electrodes for use in the method of the invention;

FIGS. 4A, 4B, 4C, 4D and 4E illustrate various forms of probe electrodes for use with the present invention;

DETAILED DESCRIPTION

Figure 1A:
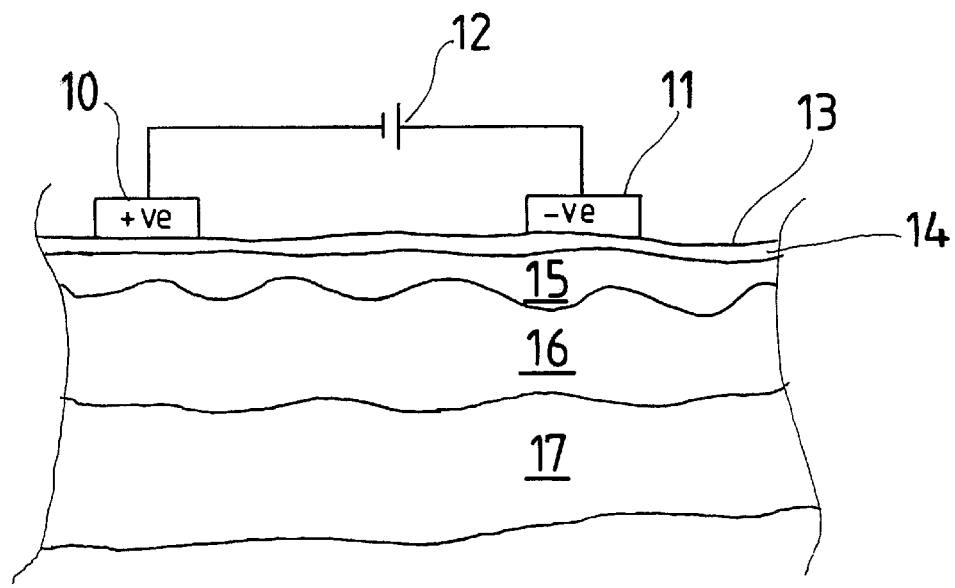
FIG. 1A is a schematic drawing illustrating a conventional iontophoresis method where the two electrodes are placed adjacent each other on a skin surface as described above.

In FIG. 1A, there is shown a conventional method of iontophoresis delivery wherein electrodes 10 and 11 are electrically connected to battery 12. Each electrode 10 and 11 is applied to skin surface 13 and there is also shown epidermis layer 14, dermis. layer 15, subcutaneous fat layer 16, muscle layer 17 and deep tissue layer 18.

Figure 1B:
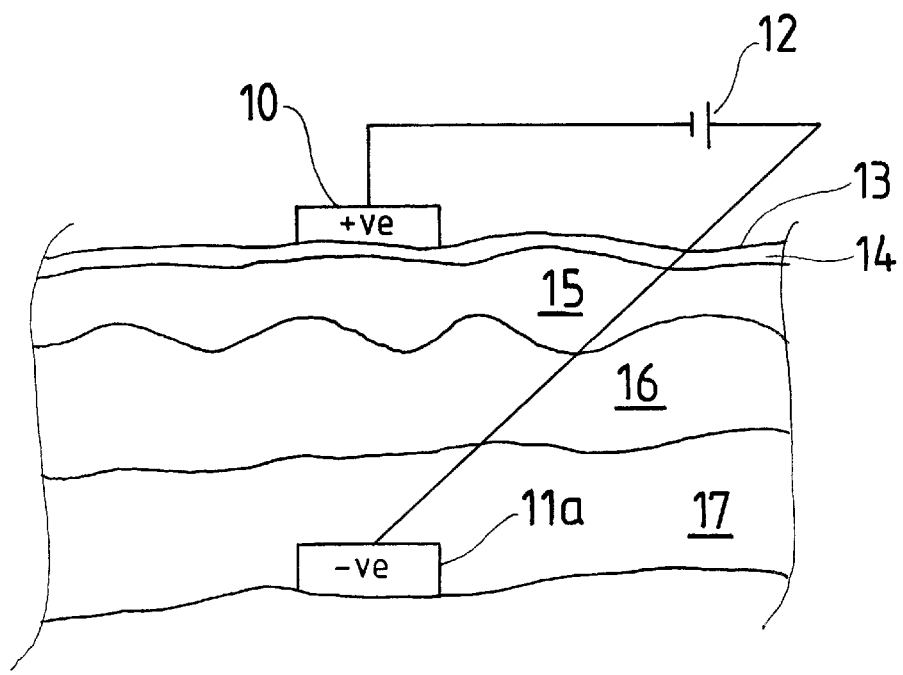
FIG. 1B is a schematic drawing illustrating the iontophoresis method of the invention.

In FIG. 1B, in contrast, the electrodes 10 and 11a have been placed so that a layer of tissue is interposed or sandwiched therebetween in accordance with the invention whereby delivery of active substance in accordance with the required concentration may be facilitated to the target tissue. Electrode 11a is a needle electrode.

Figure 1C:
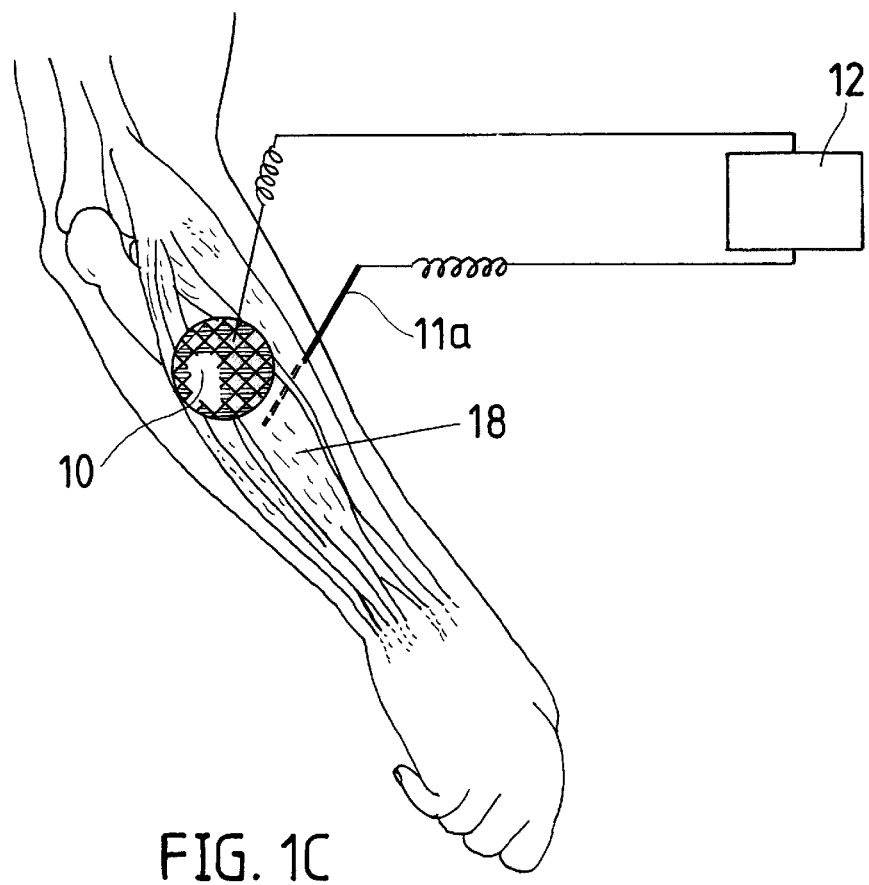
FIG. 1C is a drawing illustrating the application of the method of FIG. 1B to deep muscle delivery.

In FIG. 1C, there is shown an application of the method of FIG. 1B for delivery of active substance in the required concentration to deep muscle layer 18 which is outside the scope of the invention but which is included for the sake of convenience. There is also utilised an electrode 10 in the form of a skin pad containing a drug to be delivered to deep muscle layer 18 as well as needle electrode 11a.

Figure 1D:
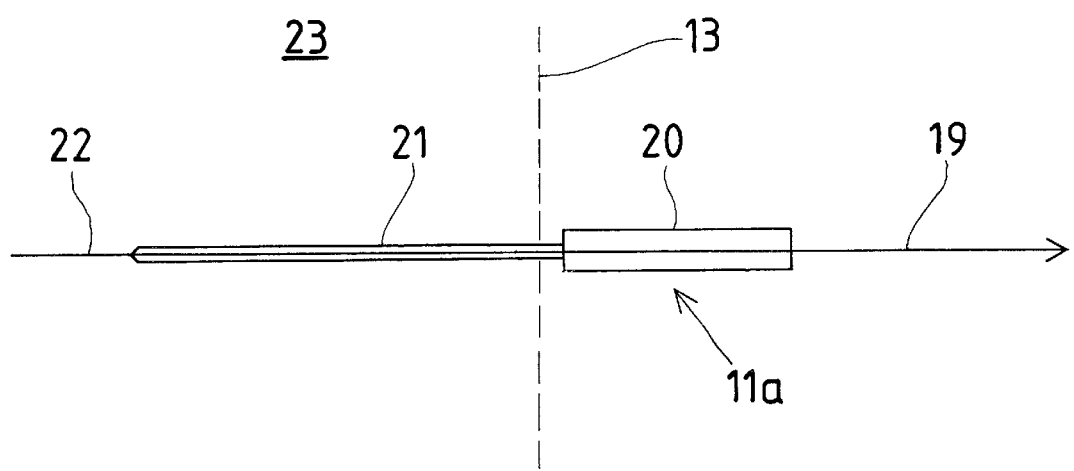
FIG. 1D represents a schematic form of a needle electrode for use in the method of the invention.

In FIG. 1D, there is shown needle electrode 11a including insulated wire 19, electrode body 20, insulating sheath 21 and needle tip 22. The insulated wire is electrically connected to a source of electrical power (not shown) and the donor electrode (not shown). The needle electrode is shown inserted into a tissue layer 23 through skin surface 13.

Figure 1F:
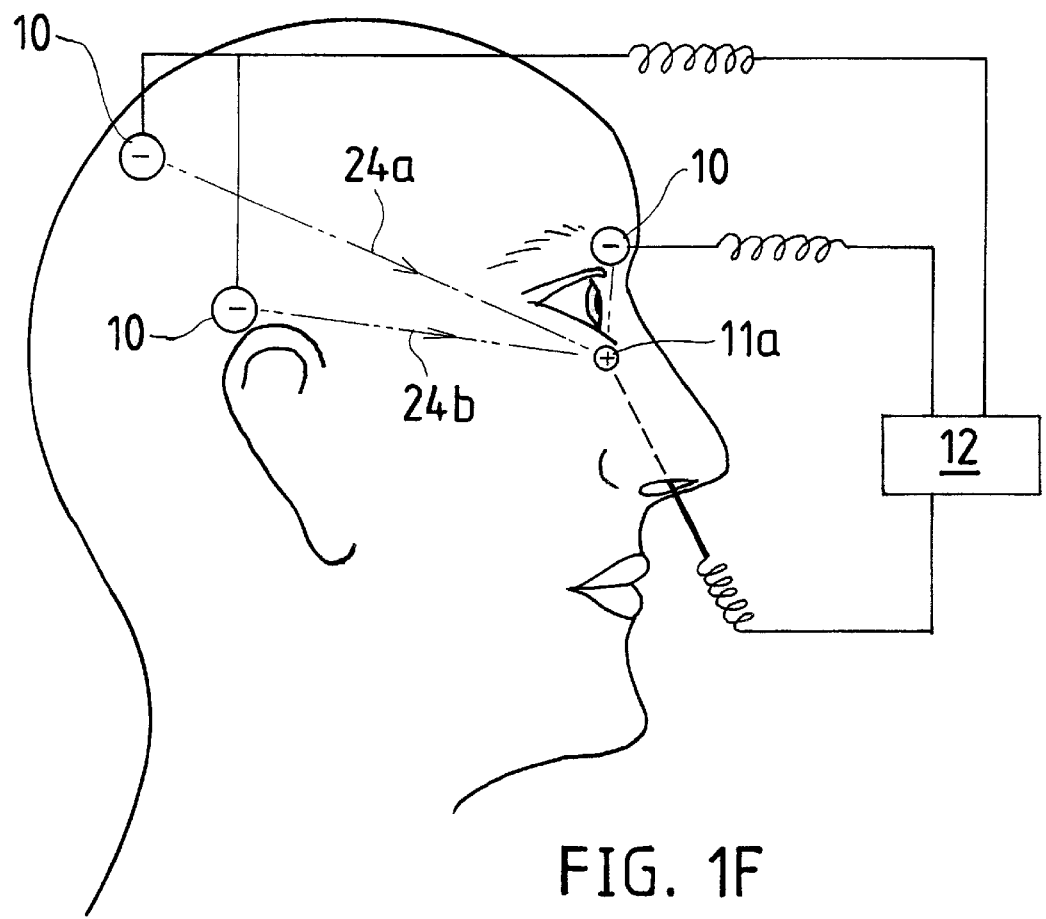
FIG. 1F represents a front view of the embodiment shown in FIG. 1E.
Figure 1E:
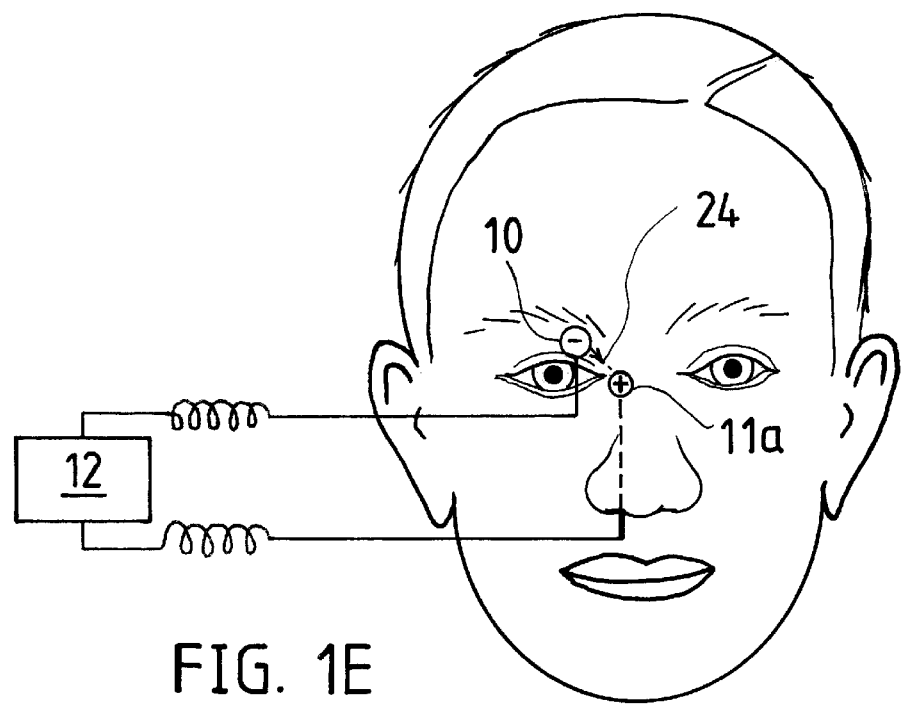
FIG. 1E represents a side view of the invention to delivering active substance to the ear, nose or throat.

In FIG. 1E, there is shown an iontophoretic method of the invention as applied to delivery of a drug to the ear, nose or throat or ophthalmic delivery. Again, there is utilised skin pad electrode 10 and needle electrode 11a. Electrode 10 is applied to the eye and electrode 11a is inserted in the nasal passage. The path of the current is shown by the line 24 in phantom.

In FIG. 1F, there is shown three alternative positions for electrode 10 which may occur on the eye, adjacent the ear, or above the ear as shown by the various locations designated 10. There is also shown current paths 24a and 24b which are applicable.

In FIGS. 2A through 2F, there are shown various kinds of needle electrodes that may be used in the iontophoretic method of the invention.

FIG. 2A shows two types of needle 25 and electrode body 26. FIG. 2B illustrates an ovoid body, FIG. 2C illustrates a curved body, FIG. 2D illustrates a hollow loop body, FIG. 2E illustrates a body 26 provided with a hook 27 and FIG. 2F shows a flat filled loop body.

Figure 3A:
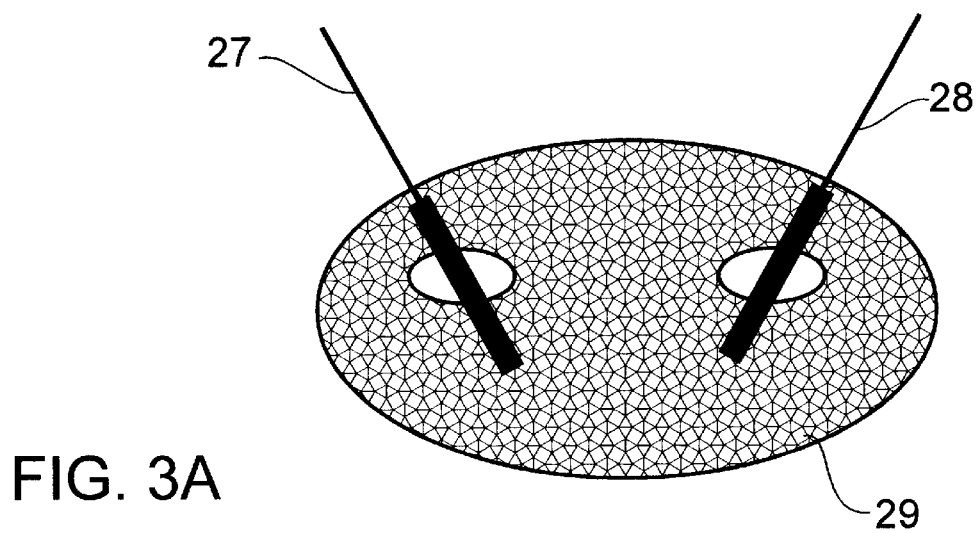
FIGS. 3A, 3B and 3C illustrate various forms of placement of electrodes in the method of the invention.
Figure 3B:
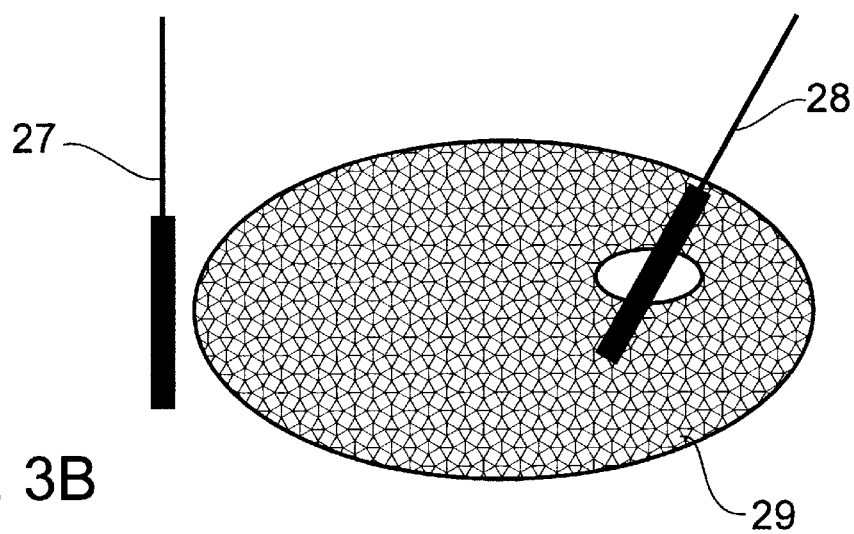
Figure 3C:
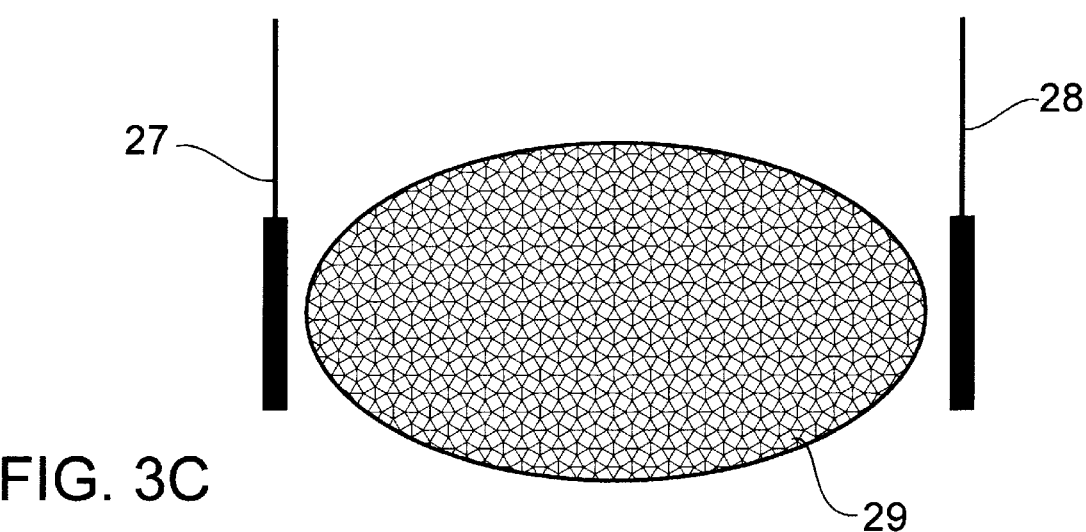

FIGS. 3A through 3C illustrate the possible combinations of placement positions for donor and receptor electrodes for direct tissue delivery in accordance with the method of the invention.

In FIG. 3A, there is shown a situation where both electrodes 27 and 28 penetrate target tissue 29. Electrodes 27 and 28 may be either the donor or receptor electrode. Target tissue 29 may include any particular tissue, organ, tumor, injured, infected or diseased site within or outside the body as shown in FIGS. 1E and 1F.

In FIG. 3B, electrode 27 is located outside target tissue 29 and one electrode 28 penetrates target tissue 29.

In FIG. 3C, both electrodes 27 and 28 are located adjacent to target tissue 29.

In each of the cases shown in FIGS. 3A through 3C, electrodes 27 and 28 may comprise a needle electrode, static probe, micro dialysis tubing or probe, conventional surface electrode, any surgically implanted electrode or conducting material introduced into the tissue on its surface or on the outside of the body.

In FIGS. 4A through 4E, there are shown various kinds of rigid probe electrodes for use with the method of the invention.

In FIG. 4A, there is shown probe 30 having insulating handle 31, conductor or electrode 32 which is connected to a power source (not shown), insulation 32a, probe body 33 and compartment 34 for containing a drug solution which may emerge from holes or perforations 35 on compartment 34 when current is applied.

FIG. 4B shows a similar probe electrode to that shown in FIG. 4A with the exception that compartment 34 is longer and confined to one side of the body 33.

FIG. 4C shows a similar probe electrode to FIG. 4A with the exception that compartment 34 is longer when compared to compartment 34 in FIG. 4A.

FIG. 4D shows a detachable sheath 36 having a tip 37 and holes 35 and resilient tube or sleeve 38 which is adapted to fit over probe body 39 shown in FIG. 4E which has electrode 32 associated therewith as well as insulating handle 31. Electrode 32 has end 32b which extends beyond body 33 as shown and into sheath 36 to provide compartment 34.

It will also be appreciated that probe body 33 may be flexible or resilient if desired or alternatively, may be made from rigid material. The compartment 34 may be made as long as may be desired and may even extend to the insulating handle 31 if required.

Figure 5:
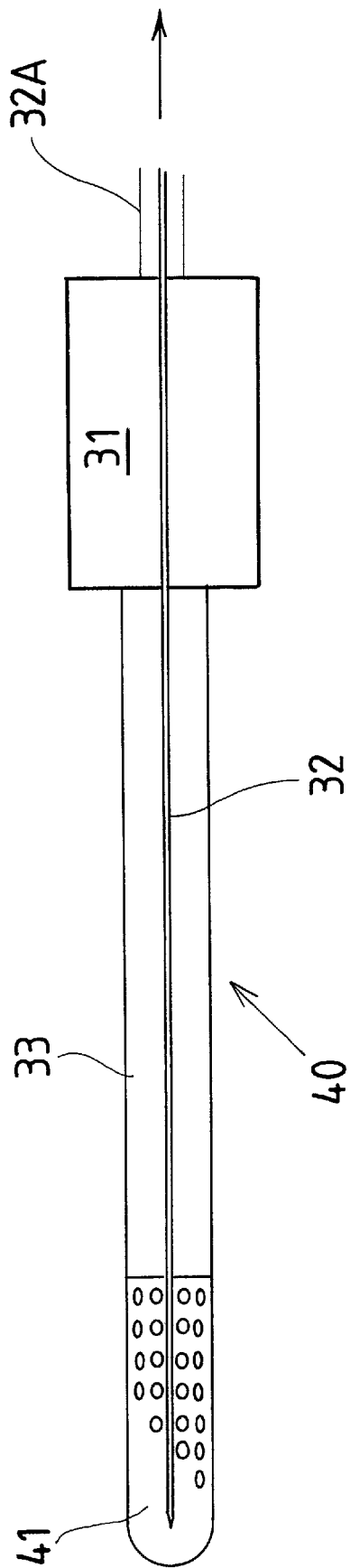
FIG. 5 represents a specific form of probe electrode for use with the present invention.

In FIG. 5, there is shown another type of probe electrode 40 which is provided with a dialysis membrane 41 if desired which covers compartment 34. The probe electrode 40 may have a flexible or rigid body or casing 33. The dialysis membrane may be from 1–3 cm long and may be modified for one-sided delivery as shown in FIG. 4B or both sides as shown in FIG. 4C.

EXPERIMENTAL SECTION

Chemicals and Instruments:

[$^{14}$C]Lignocaine HCI (specific activity 48 mCi/mmol, purity >97%) and [$^3$H]Ethanolamine (specific gravity 35 mCi/mmol) were purchased from either New England Nuclear, c/—DuPont (Australia) Ltd., Sydney or Amersham Australia Pty. Ltd., Sydney. Tissue solubiliser, NCSII, and liquid scintillation cocktails (OCS and Emulsifier-Safe) were purchased from Amersham Australia Pty. Ltd., Sydney. HEPES (N-2-hydroxyethylpiperazine-N-2-ethanesulphonic acid) buffer salt was purchased from Sigma Australia, Sydney and all other chemical reagents were of analytical grade. A liquid scintillation counter (Tri-carb® 4000 series, United Technologies Packard, USA) was used to determine the radioactivity in the samples. The constant current used in the experiments was generated by a custom-made constant-current source.

Animals:

Male Wistar rats (300–350 g) were used in the studies. The animals were housed under standard laboratory conditions (20.0±0.5° C., relative humidity 55–75%) and supplied with a normal pellet diet and water ad libitum. All experiments had previously been approved by the Animal Experimentation Committee of the University of Queensland.

In Vivo Epidermal Penetration and Local Tissue Uptake Studies:

The rats were lightly anaesthetised with sodium pentobarbitone (60 mg/kg ip.) or ketamine (130.5 mg/kg)/azaperone (75 mg/kg) mixture and their body temperature was maintained throughout the experiment at 37° C. by placing them on a heating pad. The hair on the dorsal area was clipped with electrical clippers, and any residual hair was removed by application of a depilatory cream (Singh & Roberts, 1993) [Nair; Carter-Wallace (Australia) Pty. Ltd.). The depilatory area was swabbed with a mixture of distilled and deionised water and methyl alcohol (Singh & Roberts, 1993) to remove any traces of the depilatory. A donor glass absorption cell (internal diameter, 1.8 cm) was fixed to the epidermis using adhesive. The glass cell was warmed to 37° C. by means of an external heating device (Siddiqui et al., 1985). A 2 ml solution of 50 mM HEPES buffer, pH 6.3 spiked with [$^{14}$C]lignocaine and [$^3$H]ethanolamine was placed in the donor solution. The solution was stirred by a glass stirrer driven by an external motor. A silver electrode (anode) was placed in the donor cell and the circuit completed by placement of a receptor electrode as described later. A current of 0.38 mA/cm$^2$ was applied between the two electrodes. Samples (10 μl) were removed from the donor cell at 0,15,30,45,60,90,120 min and placed in scintillation vials. The glass cell was removed from the rat skin at 2 hr after commencement of the experiment, and the application area was wiped dry with blotting paper. A blood sample was then taken from the heart, and the animals sacrificed with overdose anaesthetic ether. Immediately thereafter the tissues below the treated with, i.e., skin, subcutaneous tissue, muscle lining or superficial muscle, muscle and fat pad were removed by dissection and placed in preweighted scintillation vials (Singh & Roberts, 1993). Similarly, the tissues below the contralateral side were also removed. Dissection instruments were cleaned with alcohol soaked swabs between each tissue sample to prevent cross contamination of radiation. Epidermal and dermal layers were separated by exposure to concentrated ammonia fumes following the method of Kligman and Christophers (1963).

Receptor Electrode Placement

Part A:

A dermal absorption cell was affixed to the skin of the rat, 7 cm or directly adjacent to the donor cell. A solution of 2 mL 20 mM HEPES was placed in this receptor cell and the circuit completed.

Part B:

While the rat was anaesthetized, an incision was made on the abdomen of the rat. An IOMED® receptor was inserted into the abdomen, against the abdominal muscle layer directly beneath the donor electrode site. Parafilm® was placed on the rats organ to provide protection from the receptor. The rat abdomen was then sutured, and the rat tested 1 hr to allow the blood supply to stabilise before commencement of iontophoresis.

Sample Treatment:

Aqueous samples removed from the glass cell were directly mixed with 5 ml of liquid scintillation cocktail Emulsifier-Safe and counted on liquid scintillation counter. The tissue samples were solubilised with 1 ml of tissue solubiliser NCSII at 50° C. for 6–8 hrs, longer where required, prior to the addition of 10 ml of organic scintillant OCS for scintillation counting.

Analysis:

Zero-time samples from the cell were used to represent the initial solution concentration, and radioactivity in the tissues and plasma were converted to a fraction of the initial solution concentration (concentration fraction).

Results and Discussion

Figure 6:
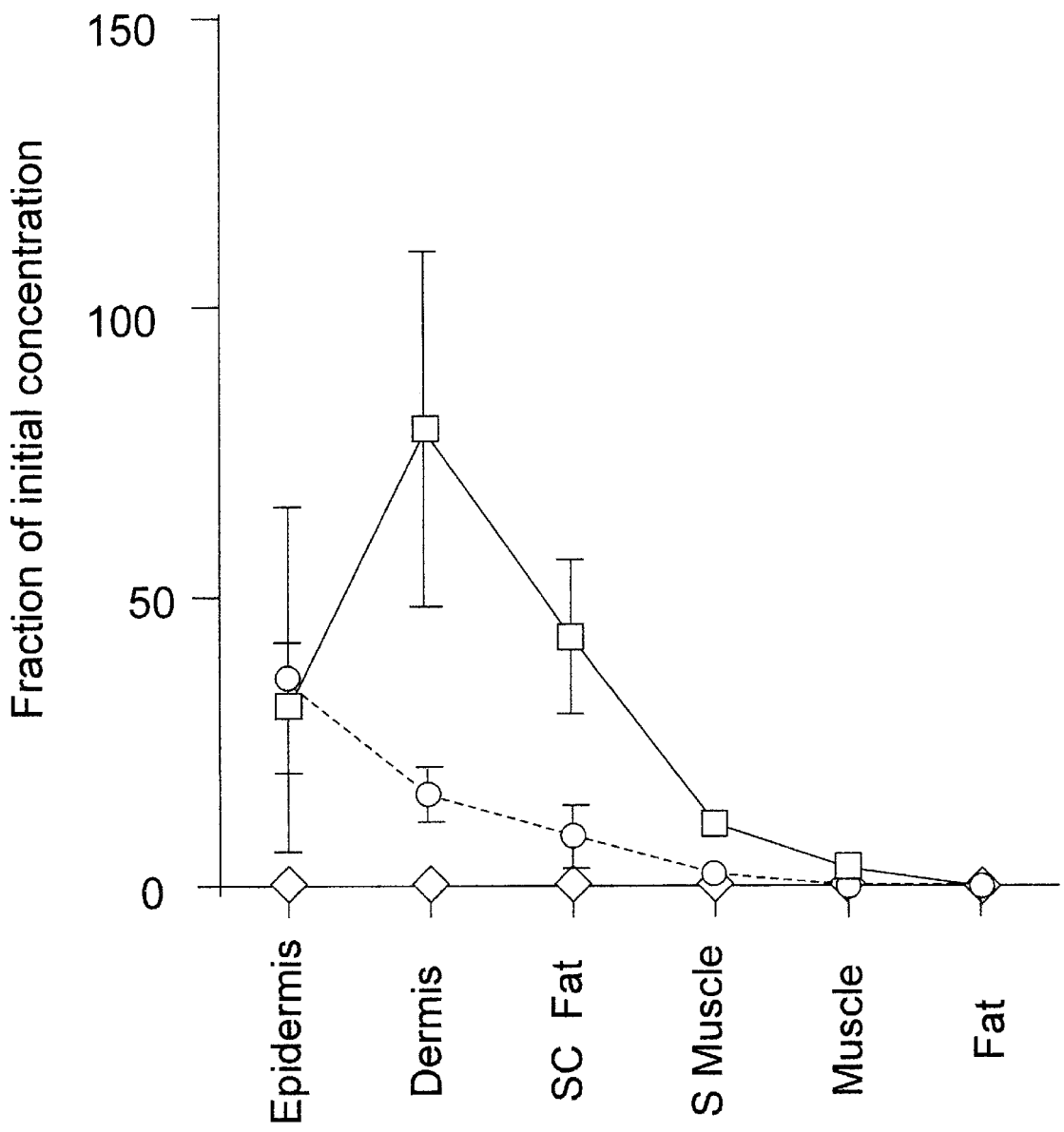
FIGS. 6 and 7 compare the method of "sandwich" placement of electrodes in accordance with the method of the invention compared to conventional placement of electrodes as described in more detail in the EXPERIMENTAL SECTION.
Figure 7:
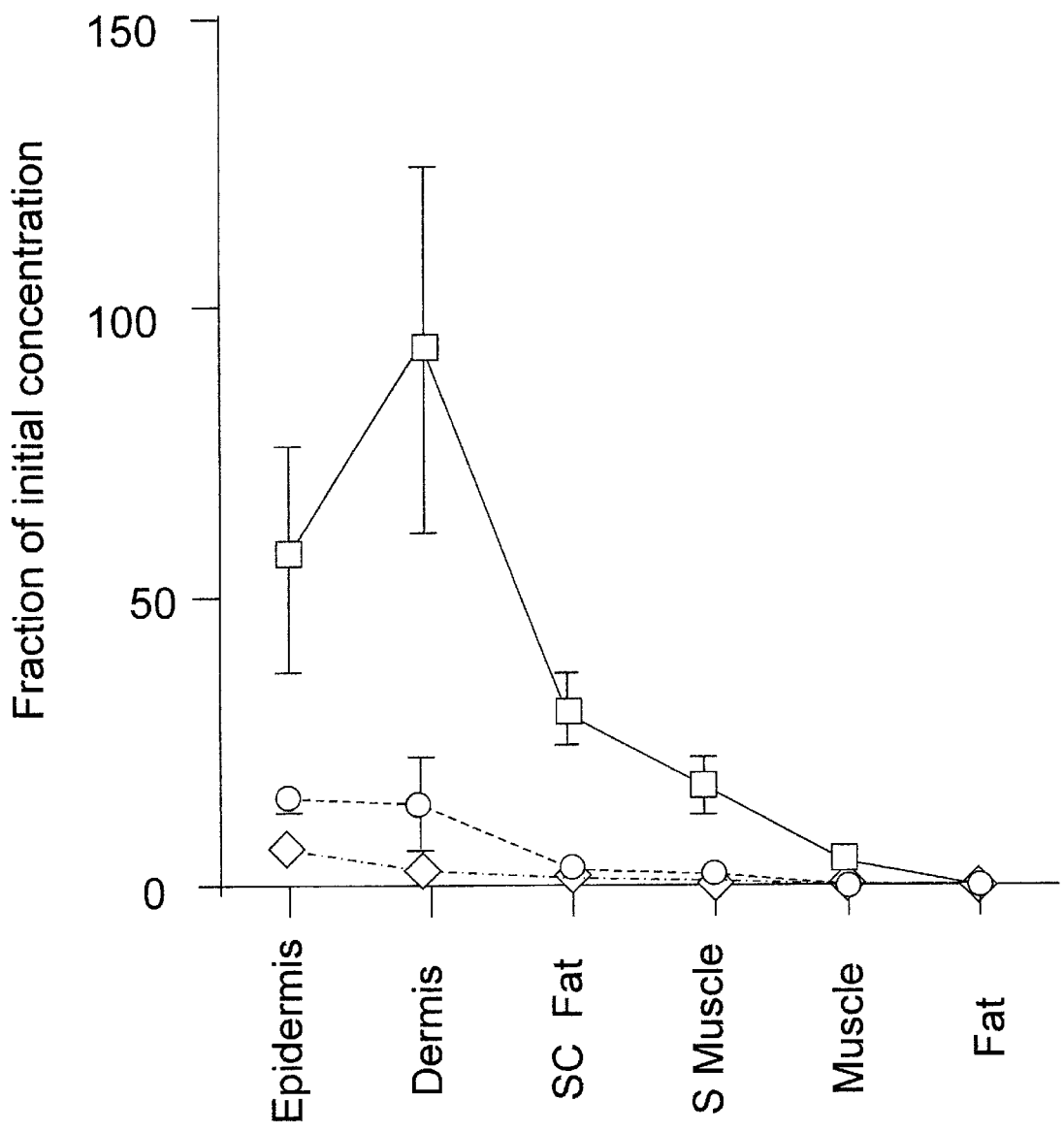

FIGS. 6 and 7 compares the "sandwich" placement of electrodes with conventional placement of electrodes, that is, side-by-side, on the surface of the skin, of lignocaine and ethanolamine, respectively.

When electrodes are placed adjacent to each other on the skin of a subject, the path of solutes or active substance follows that of least resistance, that is, through the dermis. However, when electrodes are placed in this "sandwich" form, a higher concentration of solute ions or active substances in deeper tissues directly beneath the electrode is observed and it is also noted that at a distance corresponding to the spacing between the epidermis and the abdominal muscle layer that the delivery of active substance has maximum penetration.

1. Bagniefski, T. and Burnette, R. R., 1990, *J. Controlled Release* 11 113–122
2. Bellatone, N. H.; Rim, S.; Francoeur, M. L. and Rasadi, B., 1986, *Int. J. Pharmacol.* 30 63–72
3. Burnette et al, 1988, *J. Pharm. Sci.*, 77 132–137
4. Burnette, R. R. and Marrero, D., 1986, *J. Pharm. Sci.* 5 738–743
5. Burnette, R. R. and Ongpipattanakul, B., 1987, *J. Pharm. Sci.*, 76 765–773
6. Chien et al., 1989, *J. Pharm. Sci.*, 78 376–383
7. DelTerzo et aL, 1989, *Pharm. Res.*, 6 85–90
8. DeNuzzio, J. D. and Berner, B., 1989, *J. Controlled Release*, 11 105–112
9. Feldman, R. J. and Maibach, H. l., 1967, *Arch. Dermatol.* 48 181–183
10. Gangarosa et al., 1980, *J. Pharm. Exp. Ther.*, 212 377–381
11. Kasting, G. B. and Keister, J. C., 1989, *J. Controlled Release*, 8 195–210
12. Kligman, A. M. & Christophers, E., 1963, *Arch. Dermatol.*, 88 702–705
13. Lelawongs et al., 1990, *Int. J, Pharm.*, 61 179–188
14. Masada et al., 1989, *Int. J. Pharm.*, 49 57–62
15. O'Malley, E. P. and Oester, Y. T., 1955, *Arch. Phys. Med. Rehabil.*, 36 310–316
16. Okabe et al., 1986, *Controlled Release*, 4 79–85
17. Phipps et al., 1989, *J. Pharm. Sci.*, 78 365–369
18. Pikal, M. J., 1990, *Pharm. Res.*, 7 213–221
19. Pikal, M. J. and Shah, 1991, *S. Pharm. Res.*, 7 222–229
20. Potts et al., 1984, *J. Invest. Dermatol.*, 82 97
21. Roberts et al., 1982, *Aust. N.Z. J. Med.*, 12 305–306
22. Siddiqui et al., 1985b, *J. Pharm. Pharmacol.*, 37 732–735
23. Siddiqui et al., 1985, *Int. J. Pharm.*, 27 193–203
4. Siddiqui et al., 1989, *J. Pharm. Pharmacol.*, 41 430–432
25. Singh et al., 1993, *J. Pharm. Sci* 82 127–131
26. Srinvasan et al., 1989, *J. Pharm. Sci.* 78 370–375
27. Srinvasan, V. & Higuchi, W. l., 1993, *J. Pharm. Sci.* 82 127–131
28. Tregear, 1966, *J. Invest. Dermatol.* 46 16–23
29. Wearley et al., 1989, *J. Controlled Release* 9 231–242
30. Yamamoto, T. & Yamamoto, Y., 1976, *Med. Biol. Eng. Comp.* 14 151–158
31. Yamamoto, T. & Yamamoto, Y., 1978, *Med. Biol. Eng. Comp.* 16 592–594

LEGENDS

FIG. 6
Penetration of 3H ethanolamine into tissue. Comparison of receptor placement.

| | |
|---|---|
| —□— | treated tissue - cells positioned "sandwich" style |
| ····◇···· | contralateral tissue - cells positioned "sandwich" style |
| ---○--- | treated tissue - cells positioned adjacently on surface of skin |
| ---△--- | contralateral tissue - cells positioned adjacently on surface of skin |

FIG. 7
Penetration of 14C lignocaine into tissue. Comparison of receptor placement.

| | |
|---|---|
| —□— | treated tissue - cells positioned "sandwich" style |
| ····◇···· | contralateral tissue - cells positioned "sandwich" style |
| ---○--- | treated tissue - cells positioned adjacently on surface of skin |
| ---△--- | contralateral tissue - cells positioned adjacently on surface of skin |

We claim:

1. A method of administration of an active substance to a sensitive target tissue selected from the eye, ear, nose or throat which includes the steps of:
    (i) inserting a first electrode into a nasal passage of a subject and applying a second electrode to the subject adjacent the eye or adjacent the ear wherein said first and second electrodes are each electrically connected to a power source and said target tissue is sandwiched between each of said electrodes to achieve a current path which is of minimal electrical resistance and
    (ii) delivering said active substance to said target tissue.
2. A method as claimed in claim 1 wherein the first electrode is a donor electrode and the second electrode is a receptor electrode.
3. A method as claimed in claim 2 wherein the donor electrode is a needle electrode.
4. A method as claimed in claim 2 wherein the donor electrode is a probe electrode.
5. A method as claimed in claim 2 wherein the donor electrode is a pad for topical administration.
6. A method as claimed in claim 2, wherein the donor electrode includes an electrode body formed from insulating material, a conductor passing through the electrode body and a compartment for storage of active substance located adjacent an outer end of the electrode body which is provided with access means whereby active substance can be delivered to adjacent tissue.
7. A method as claimed in claim 6 wherein the access means includes apertures in an external wall of the compartment.
8. A method as claimed in claim 6 wherein the access means includes dialysis membrane or porous membrane adjacent to the compartment.
9. A method as claimed in claim 6 wherein the electrode body has an outwardly extending conductor part or needle tip adjacent an outer end of the electrode body.
10. A method as claimed in claim 6 also including an insulating handle.
11. A method as claimed in claim 1 wherein the target tissue is the eye.
12. A method as claimed in claim 1 wherein the target tissue is the ear.
13. A method as claimed in claim 1 wherein the target tissue is the throat.
14. A method as claimed in claim 1 wherein the target tissue is the nose.

\* \* \* \* \*